United States Patent

Lüddecke et al.

[11] Patent Number: 5,863,953
[45] Date of Patent: Jan. 26, 1999

[54] LIQUID, OIL-MISCIBLE CAROTENOID PREPARATIONS

[75] Inventors: Erik Lüddecke, Mutterstadt; Angelika-Maria Pfeiffer, Oldenburg; Joachim Meyer, Maxdorf, all of Germany

[73] Assignee: BASF Aktiengesellschaft, Ludwigshafen, Germany

[21] Appl. No.: 972,392

[22] Filed: Nov. 18, 1997

[30] Foreign Application Priority Data

Nov. 27, 1996 [DE] Germany .................. 196 49 062.6

[51] Int. Cl.$^6$ ........................... A61K 31/07; A61K 31/12
[52] U.S. Cl. ..................... 514/691; 514/725; 514/763; 514/937
[58] Field of Search .................... 514/691, 725, 514/763, 937

[56] References Cited

U.S. PATENT DOCUMENTS 3,998,759 12/1976 Hoekstra ...................... 252/466 PT
4,522,743 6/1985 Horn et al. ............................ 252/311

FOREIGN PATENT DOCUMENTS

| 10708/88 | 7/1988 | Australia . |
| 65 193 | 11/1982 | European Pat. Off. . |
| 278 284 | 8/1988 | European Pat. Off. . |
| 25 34 091 | 2/1976 | Germany . |
| 37 02 030 | 8/1988 | Germany . |
| 993 138 | 5/1965 | United Kingdom . |
| 94/19411 | 9/1994 | WIPO . |
| 96/23420 | 8/1996 | WIPO . |

OTHER PUBLICATIONS

Int. Ency. of Food and Nutrion, No. 9, 134–139 and 129–131.

*Primary Examiner*—Leonard Schenkman
*Attorney, Agent, or Firm*—Keil & Weinkauf

[57] ABSTRACT

Liquid, oil-miscible carotenoid preparations which, as double dispersion systems, comprise an aqueous-disperse phase which has a particle diameter of less than 100 µm and in which particles, stabilized by protective colloid, of one or more carotenoids are present in disperse form, in an oil as a dispersion medium.

14 Claims, No Drawings

LIQUID, OIL-MISCIBLE CAROTENOID PREPARATIONS

Liquid, oil-miscible carotenoid preparations.

The invention relates to liquid, oil-miscible carotenoid preparations, processes for preparing these, and to their use as an additive for animal feeds, foods, cosmetics and pharmaceuticals.

Carotenoids form a group of colored pigments having hues from yellow to red, which occur widely in nature and impart a characteristic color to many foods. Among the most important representatives to be mentioned of this category of substances are β-carotene, astaxanthin, β-apo-8'-carotenal, canthaxanthin, lycopene and citranaxanthin. Both for the food and feed industry and for pharmaceutical technology, these synthetically obtainable substances represent important colorants, eg. as a substitute for synthetic dyes, some of them being of interest because of their provitamin A activity.

All carotenoids are insoluble in water, whereas some solubility, albeit only small, is found in fats and oils. This limited solubility and the high sensitivity to oxidation impede a direct application of the relatively coarse products obtained in the synthesis to coloring foods and feeds, since the substances in coarsely crystalline form are absorbed but poorly and therefore yield only poor coloring results.

Improved color yields in the direct coloring of foods can only be achieved by systematically prepared formulations in which the active ingredients are present in finely disperse form and, if required, are protected against oxidation by protective colloids. Moreover, these formulations used in feeds result in higher bioavailability of the carotenoids and thus indirectly in better coloration effects, eg. in the pigmenting of egg yolks or fish.

In the feed industry, especially in the fish farming sector, it is particularly astaxanthin and canthaxanthin from the carotenoid group, which are used for coloring, inter alia, salmon, trout and shrimps. In so doing, the active ingredients are used in the form of dry powders in which the dispersed carotenoid is protected against oxidative degradation by eg. gelatin and sugar acting as protective colloids. In the process of feed production, the dry powder is directly incorporated in an extrusion or pelleting process, the stress factors such as heat, humidity and influence of air, which are obtained under the production conditions often resulting in undesirable damage to the product and consequently in losses in active ingredient.

To reduce these losses in active ingredient it is possible, as described in WO 96/23420, for finely ground astaxanthin to be suspended in oil and then to be sprayed onto the feed after the latter has been extruded or pelleted. Neither the bioavailability and consequently the coloring effect achieved nor the chemical stability of the active ingredients are satisfactory in this case.

In other processes, described in WO 94/19411, crystalline β-carotene is ground in the presence of an aqueous protective colloid solution and then, by brief heating up to the melting point, is converted into an amorphous modification.

This formulation and the frequently described aqueous carotenoid dispersions and o/w emulsions, in which the active ingredient exists in the presence of stabilizing protective colloids are likewise unsuitable, since they are immiscible with oils.

GB 993 138 describes a process for preparing, inter alia, vitamin A-containing beadlets, which comprises vitamin A being dispersed in an aqueous, gelatin-containing protective-colloid solution and this dispersion being precipitated in the form of beadlets by being additionally suspended in oil. Owing to unduly large particle diameters of above 300 μm and the attendant physical instability of such suspensions or emulsions, such systems are unsuitable for the abovementioned application of liquid carotenoid preparations.

It is therefore the object of the invention to develop carotenoid formulations which do not have the abovementioned drawbacks.

We have found that this object is achieved, according to the invention, with the provision of liquid, oil-miscible carotenoid preparations which, as double dispersion systems, comprise an aqueous-disperse phase which has a particle diameter of less than 100 μm and in which particles, stabilized by protective colloid, of one or more carotenoids are present in disperse form, in an oil as a dispersion medium.

The invention also relates to a process for preparing liquid, oil-miscible carotenoid preparations, wherein an aqueous, protective colloid-containing dispersion of one or more carotenoids is emulsified in oil in the presence of an emulsifier.

The novel combination of aqueous dispersing processes of fat-soluble active ingredients with a further water-in-oil emulsifying step allows products to be obtained which have novel, surprising property profiles.

The liquid carotenoid preparations thus obtainable are eminently suitable as dyes or additives for foods and/or feeds and for cosmetic or pharmaceutical dosage forms.

The preparation of the aqueous-disperse phase, which contains particles, stabilized by protective colloid, of one or more carotenoids has formed the subject of numerous previous publications and patents, such as EP-B-0 278 284, EP-B-0 065 193, DE-A-3 702 030, DE-A-2 534 091 and of a summary in R. A. Morton, Fat Soluble Vitamins, Intern. Encyclopedia of Food and Nutrition, Vol. 9, Pergamon Press 1970, pp. 134–139.

Of the many aqueous dispersing methods cited above, the micronization method according to EP-B-0 065 193 is particularly suitable for the purpose in hand. This method is distinguished in that a carotenoid is dissolved in less than 10 seconds in a volatile, water-miscible organic solvent at between 50° C. and 200° C., and the carotenoid is immediately precipitated in colloidal-disperse form from the solution obtained by rapid mixing with an aqueous protective-colloid solution. For details see EP-B-0 065 193.

The carotenoids which can be used within the scope of the invention are the known accessible natural or synthetic representatives of this class of compounds, which are suitable as colorants, eg. β-carotene, astaxanthin, lycopene, bixin, zeaxanthin, cryptoxanthin, citranaxanthin, lutein, canthaxanthin, β-apo-4'-carotenal, β-apo-8'-carotenal, β-apo-12'-carotenal, β-apo-8'-carotenoic acid and esters of hydroxy- and carboxy-containing representatives of this group, eg. the lower alkyl esters and preferably the methyl and ethyl esters. Particular preference is given to the industrially hitherto readily accessible carotenoids such as β-carotene, astaxanthin, canthaxanthin, lycopene, β-apo-8'-carotenal and β-apo-8'-carotenoic acid esters, used on their own or as a mixture, where the active ingredients are present in oily, amorphous and/or crystalline form, the oily and amorphous modifications being preferred with a view to optimal bioavailability.

In pursuance of the abovementioned micronization method, the first dispersing step as part of the overall process can be carried out, in particular, with water-miscible, thermally stable, volatile solvents containing only carbon, hydrogen and oxygen, such as alcohols, ethers, esters, ketones and acetals.

Preferentially used are ethanol, n-propanol, isopropanol, 1-methoxy-2-butanol, 1-n-propoxy-2-propanol or acetone. Generally, those solvents are expediently used which are water-miscible to at least 10%, have a boiling point lower than 200° C. and/or contain fewer than 10 carbon atoms.

Examples of protective colloids are gelatin, fish gelatin, starch, dextrin, vegetable proteins, pectin, gum arabic, casein, caseinate or mixtures thereof. Equally, however, poly(vinyl alcohol), poly(vinylpyrrolidone), methylcellulose, carboxymethylcellulose, hydroxypropylcellulose and alginates can be used. For further details see R. A. Morton, Fat Soluble Vitamins, Intern. Encyclopedia of Food and Nutrition, Vol. 9, Pergamon Press 1970, pp. 128–131. To increase the mechanical stability of the end product the colloid is expediently admixed with a plasticizer such as sugar or sugar alcohols, eg. sucrose, glucose, lactose, invert sugar, sorbitol, mannitol or glycerol.

The amounts of protective colloid, plasticizer and carotenoid are generally chosen so as to give an end product which comprises from 0.01 to 10 wt. %, preferably from 0.5 to 5 wt. %, of carotenoid, from 2 to 20 wt. % of a protective colloid, from 2 to 20 wt. % of a plasticizer, all percentages based on the total mass of the finished emulsion, and possibly small amounts of a stabilizer.

To increase the stability of the active ingredient against oxidative degradation, stabilizers such as α-tocopherol, t-butylhydroxytoluene, t-butylhydroxyanisole, ascorbic acid or ethoxyquin are added advantageously. They may either be added to the aqueous or the solvent phase, but are preferentially codissolved with the dyes and any additional emulsifiers in the solvent phase.

Examples of emulsifiers which can be used for the primary dispersion include ascorbyl palmitate, polyglycerol fatty acid esters, sorbitan fatty acid esters, propylene glycol fatty acid esters or lecithin in a concentration of from 0 to 200 wt. %, preferably from 10 to 150 wt. %, particularly preferably from 15 to 80 wt. %, based on the carotenoid(s).

By adding preservatives permitted in the food and feed industry, for example ascorbic acid, sodium sorbate, benzoic acid, sodium benzoate or PHB esters such as methyl 4-hydroxybenzoate or propyl 4-hydroxybenzoate in a concentration of from 0 to 200 wt. %, preferably from 10 to 150 wt. %, particularly preferably from 15 to 80 wt. %, based on the carotenoid(s) is possible to prevent undesirable microbial decomposition of the aqueous dispersion.

In some cases it may also be advantageous to dissolve not only the carotenoid or the mixture of a plurality of carotenoids in the first dispersing step, but also a physiologically permitted oil such as sesame oil, corn oil, cottonseed oil, soybean oil or peanut oil and esters of medium-length chain vegetable fatty acids in a concentration of from 0 to 500 wt. %, preferably from 10 to 300 wt. %, particularly preferably from 20 to 100 wt. %, based on the carotenoid(s), which oil is then coprecipitated, in extremely finely disperse form, with the active ingredients and said additives upon mixing with the aqueous phase.

Depending on the type and quantity of the protective colloid used, the aqueous carotenoid dispersion obtained is a deeply colored, viscous liquid which, in the case of a gellable colloid solidifies like a gel and in which the mean particle size of the carotenoids is less than 0.2 mm.

Removal of the solvent can be effected, depending on the boiling point, in a manner known per se, eg. by distillation, possibly under reduced pressure, or by extraction with a solvent immiscible with water.

In contrast to the abovementioned prior art, according to which the aqueous active ingredient dispersions are converted into a dye powder, the additional water-in-oil emulsion in the novel process results in a novel liquid formulation in the form of a double dispersion.

In the process, with the use of an emulsifier, a water-in-oil emulsion is formed in which the water phase contains carotenoid nanoparticles stabilized by protective colloid. Eligible emulsifiers are w/o emulsifiers known per se with an HLB value below 10, in particular from 2 to 6 (cf. H. P. Fiedler, Lexikon der Hilfsstoffe fur Pharmazie, Kosmetik und angrenzende Gebiete, 1996, pp. 753 et seq.). Typical representatives of this class of emulsifiers are fatty acid partial esters of polyhydric alcohols, eg. glycerol monostearate or mixtures of mono-, di- and triglycerides, fatty acid partial esters of sorbitan and/or preferably fatty acid esters of polyglycerol, such as polyglycerol polyricinoleate, which are used in a concentration of from 10 to 1000 wt. %, preferably from 100 to 900 wt. %, particularly preferably from 400 to 800 wt. %, based on the carotenoid(s).

The dispersion medium may be of mineral, vegetable or animal origin. Typical representatives are edible oils, in particular sesame oil, corn oil, cottonseed oil, soybean oil or peanut oil, esters of medium-length chain vegetable fatty acids, and various fish oils such as mackerel oil, sprat oil or salmon oil. The amount of the dispersion medium is generally from 30 to 95, preferably from 50 to 80 wt. %, based on the total mass of the finished emulsion.

The emulsification can be carried out continuously or batchwise.

The physical stability of the double dispersion system, for example the sedimentation stability, is achieved by very good fine dispersion of the water phase in the oil phase, eg. by intensive treatment with a rotor/stator disperser at from 20° to 80°, preferably from 40° to 70° C., or with a high-pressure homogenizer such as an APV Gaulin or with a superhigh-pressure homogenizer such as the microfluidizer in the pressure range of from 700 to 1000 bar. The mean diameters thus achievable for the aqueous-disperse phase are less than 100 $\mu$m, preferably less than 10 $\mu$m, in particular less than 1 $\mu$m.

The nanoparticle carotenoids, stabilized by protective colloid, in the disperse phase moreover ensure that this liquid formulation has the same bioavailability and chemical stability as the dry powders in accordance with EP-B-0 065 193.

For coloring purposes in aquaculture, the novel liquid formulations thus prepared of carotenoid-containing active ingredients can be sprayed onto the ready-extruded fish food, either directly or as a rule after having been diluted with oils.

In the food sector, the liquid carotenoid formulations can be used for coloring, inter alia, margarine, bakery products, pasta, dessert products etc., the novel w/o emulsions being particularly suitable if the coloring process requires the formulation to be oil-soluble. From an application point of view, these liquid formulations have the additional advantage that they can be proportioned more readily than comparable carotenoid dry powders.

The same applies for the application of the novel carotenoid liquid formulations for coloring purposes in the cosmetics and pharmaceutical sector.

The following Examples explain in more detail how the novel process is carried out.

EXAMPLE 1

85 g of an astaxanthin dispersion having a mean particle diameter of the astaxanthin particles of about 100 nm, which in addition to 6 wt. % of astaxanthin contains 55 wt. % of water, 20 wt. % of sucrose, 15 wt. % of gelatin, 2 wt. % of ethoxyquin, 1 wt. % of preservatives and 1 wt. % of ascorbyl palmitate, were prepared according to the mixing-chamber micronization method in accordance with EP-B-0 065 193 and then emulsified at 50° C. for 5 minutes into a mixture of 300 g of soybean oil and 30 g of polyglycerol polyricinoleate. The resulting stable emulsion had an active ingredient content of about 1.2 wt. %.

When a toothed-ring disperser (Ultraturax®) was used as the homogenizer, mean droplet diameters of the disperse phase of about 2 μm were achieved. If, additionally, a high-pressure homogenizer (microfluidizer) was used at 1000 bar, mean droplet diameters of about 1 μm were successfully achieved.

EXAMPLE 2

193 g of an canthaxanthin dispersion having a mean particle diameter of the canthaxanthin particles of about 150 nm, which in addition to 4 wt. % of canthaxanthin contains 70 wt. % of water, 14 wt. % of sucrose, 9 wt. % of gelatin, 1 wt. % of ethoxyquin, 1 wt. % of preservatives and 1 wt. % of ascorbyl palmitate, were prepared according to the mixing-chamber micronization method in accordance with EP-B-0 065 193 and then emulsified at 60° C. for 2 minutes into a mixture of 400 g of soybean oil and 40 g of polyglycerol polyricinoleate with the aid of an Ultraturax® at 11000 rpm. To improve the fine dispersion, the emulsion was additionally homogenized at about 26° C. in two passes in a superhigh-pressure homogenizer (microfluidizer) at 900 bar. The resulting stable emulsion had an active ingredient content of about 1.2 wt. %. The mean droplet size was 0.85 μm.

We claim:

1. A liquid, oil-miscible carotenoid preparation which, as a double dispersion system, comprises an aqueous-disperse phase which has a particle diameter of less than 100 μm and in which particles, stabilized by protective colloid, of one or more carotenoids are present in dispersed form, in an edible oil as a dispersion medium.

2. The liquid, oil-miscible carotenoid preparation defined in claim 1, wherein the aqueous-disperse phase comprises particles, stabilized by protective colloid, of one or more carotenoids in oily, amorphous and/or crystalline form.

3. The liquid, oil-miscible carotenoid preparation defined in claim 1, which comprises an emulsifier with an HLB value below 10.

4. The liquid, oil-miscible carotenoid preparation defined in claim 1, wherein the aqueous-disperse phase comprises further additives such as emulsifiers, antioxidants and/or preservatives.

5. The liquid, oil-miscible carotenoid preparation defined in claim 1, wherein the particle diameter of the aqueous-disperse carotenoid-containing phase is less than 10 μm.

6. The liquid, oil-miscible carotenoid preparation defined in claim 1, which has a carotenoid content of from 0.01 to 10 weight-%.

7. A process for preparing the liquid, oil-miscible carotenoid preparation defined in claim 1, wherein an aqueous, protective colloid-containing dispersion of one or more carotenoids is emulsified in oil in the presence of an emulsifier.

8. An animal feed composition comprising the liquid, oil-miscible carotenoid preparation defined in claim 1.

9. A food composition comprising the liquid, oil-miscible carotenoid preparation defined in claim 1.

10. A cosmetic composition comprising the liquid, oil-miscible carotenoid preparation defined in claim 1.

11. A pharmaceutical composition comprising the liquid, oil-miscible carotenoid preparation defined in claim 1.

12. The liquid, oil-miscible carotenoid preparation defined in claim 1, which has an oil content of from 30 to 95 weight-%.

13. The liquid, oil-miscible carotenoid preparation defined in claim 1, which has a colloid content of from 2 to 20 weight-%.

14. The liquid, oil-miscible carotenoid preparation defined in claim 1, which has a plasticizer content of from 2 to 20 weight-%.

* * * * *